(12) United States Patent
Gumbrecht et al.

(10) Patent No.: US 10,073,107 B2
(45) Date of Patent: *Sep. 11, 2018

(54) SYSTEM FOR OPERATING A SYSTEM FOR THE INTEGRATED AND AUTOMATED ANALYSIS OF DNA OR PROTEIN

(71) Applicant: Boehringer Ingelheim Vetmedica GmbH, Ingelheim am Rhein (DE)

(72) Inventors: Walter Gumbrecht, Herzogenaurach (DE); Peter Paulicka, Erlangen (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/828,878

(22) Filed: Aug. 18, 2015

(65) Prior Publication Data

US 2016/0047832 A1 Feb. 18, 2016

Related U.S. Application Data

(63) Continuation of application No. 11/920,978, filed as application No. PCT/EP2006/062499 on May 22, 2006, now Pat. No. 9,110,044.

(30) Foreign Application Priority Data

May 25, 2005 (DE) .................. 10 2005 024 610

(51) Int. Cl.
*C12M 1/34* (2006.01)
*C12M 3/00* (2006.01)
(Continued)

(52) U.S. Cl.
CPC ...... *G01N 35/00871* (2013.01); *B01L 3/5027* (2013.01); *B01L 3/50273* (2013.01);
(Continued)

(58) Field of Classification Search
None
See application file for complete search history.

(56) References Cited

U.S. PATENT DOCUMENTS

| 5,096,669 | A | 3/1992 | Lauks et al. |
| 5,755,942 | A | 5/1998 | Zanzucchi et al. |

(Continued)

FOREIGN PATENT DOCUMENTS

| DE | 4438785 A1 | 5/1996 |
| DE | 19648695 A1 | 6/1997 |

(Continued)

OTHER PUBLICATIONS

James A. Higgins, et al., A Handheld Real Time Thermal Cycler for Bacterial Pathogen Detection, Elsevier Science B.V., Accepted Oct. 24, 2002; pp. 1115-1123.

(Continued)

*Primary Examiner* — Joseph G Dauner
(74) *Attorney, Agent, or Firm* — David S. Safran

(57) ABSTRACT

A system for the integrated and automated analysis of DNA or protein, including a single-use cartridge, with an analysis device having a control device, and devices for capturing and processing signals, the control device carrying out a completely automatic process and evaluation of molecular diagnostic analysis via single-use cartridges (Lab-on-a-Chip). Controlling of an analysis process, which occurs in the cartridge, involves the subsequent displacement and thermostatization of liquids with a first device, and with a second device the signals which are obtained during the analysis are processed. The first and the second devices are synchronized in such a manner that the analysis process of the sample can be carried out in a totally integrated manner thus producing an immediate result.

38 Claims, 9 Drawing Sheets

(51) Int. Cl.

| | |
|---|---|
| *C12Q 1/68* | (2018.01) |
| *G01N 35/00* | (2006.01) |
| *B01L 3/00* | (2006.01) |
| *B01L 7/00* | (2006.01) |
| *B01L 9/00* | (2006.01) |
| *G01N 35/08* | (2006.01) |
| *C12Q 1/686* | (2018.01) |
| *G01N 35/10* | (2006.01) |

(52) U.S. Cl.
CPC ... *B01L 3/502723* (2013.01); *B01L 3/502761* (2013.01); *B01L 7/52* (2013.01); *B01L 9/527* (2013.01); *C12Q 1/686* (2013.01); *G01N 35/00009* (2013.01); *G01N 35/00584* (2013.01); *G01N 35/00732* (2013.01); *G01N 35/08* (2013.01); *G01N 35/1002* (2013.01); *B01L 2200/027* (2013.01); *B01L 2200/0668* (2013.01); *B01L 2200/10* (2013.01); *B01L 2200/143* (2013.01); *B01L 2300/023* (2013.01); *B01L 2300/0645* (2013.01); *B01L 2300/0816* (2013.01); *B01L 2300/1822* (2013.01); *B01L 2300/1877* (2013.01); *B01L 2400/0406* (2013.01); *G01N 2035/00019* (2013.01); *G01N 2035/00346* (2013.01); *G01N 2035/00376* (2013.01); *G01N 2035/00841* (2013.01); *G01N 2035/1034* (2013.01)

(56) References Cited

U.S. PATENT DOCUMENTS

| | | | |
|---|---|---|---|
| 5,764,356 | A | 6/1998 | Iwase et al. |
| 6,054,277 | A | 4/2000 | Furcht et al. |
| 6,300,141 | B1 * | 10/2001 | Segal ............... G01N 33/54366 |
| | | | 204/228.1 |
| 6,458,325 | B1 | 10/2002 | Roscher et al. |
| 6,780,300 | B1 | 8/2004 | Alberto |
| 6,814,846 | B1 | 11/2004 | Berndt |
| 7,060,488 | B2 | 6/2006 | Duong et al. |
| 7,122,153 | B2 | 10/2006 | Ho |
| 2001/0012612 | A1 | 8/2001 | Petersen et al. |
| 2002/0019060 | A1 | 2/2002 | Petersen et al. |
| 2002/0042125 | A1 | 4/2002 | Petersen et al. |
| 2002/0142482 | A1 | 10/2002 | Wu et al. |
| 2002/0179444 | A1 | 12/2002 | Lauks |
| 2003/0073229 | A1 | 4/2003 | Greenstein et al. |
| 2003/0148530 | A1 | 8/2003 | Lauks |
| 2003/0199910 | A1 | 10/2003 | Boecker et al. |
| 2003/0207326 | A1 | 11/2003 | Su et al. |
| 2004/0029203 | A1 * | 2/2004 | Gumbrecht .......... B01J 19/0046 |
| | | | 435/7.92 |
| 2004/0086870 | A1 | 5/2004 | Tyvoll et al. |
| 2004/0115094 | A1 | 6/2004 | Gumbrecht et al. |
| 2004/0189311 | A1 | 9/2004 | Glezer et al. |
| 2004/0223874 | A1 * | 11/2004 | Numajiri .......... B01L 3/502715 |
| | | | 422/400 |
| 2004/0224339 | A1 | 11/2004 | Numajiri et al. |
| 2005/0031490 | A1 | 2/2005 | Gumbrecht et al. |
| 2009/0130658 | A1 | 5/2009 | Barlag et al. |
| 2009/0136922 | A1 | 5/2009 | Barlag et al. |

FOREIGN PATENT DOCUMENTS

| | | |
|---|---|---|
| DE | 19648441 A1 | 5/1998 |
| DE | 19928410 A1 | 1/2001 |
| DE | 10258840 A1 | 8/2003 |
| DE | 10352887 A1 | 4/2005 |
| EP | 0992287 A2 | 4/2000 |
| EP | 1203959 A1 | 5/2002 |
| EP | 1418243 A2 | 5/2004 |
| EP | 1473085 A1 | 11/2004 |
| WO | 1998022816 A1 | 5/1998 |
| WO | 1999010735 A1 | 3/1999 |
| WO | 1999044740 A1 | 9/1999 |
| WO | 1999046045 A1 | 9/1999 |
| WO | 2000052457 A1 | 9/2000 |
| WO | 2001047638 A2 | 7/2001 |
| WO | 2002072262 A1 | 9/2002 |
| WO | 2002073153 A2 | 9/2002 |
| WO | 2002097398 A2 | 12/2002 |
| WO | 2004062804 A1 | 7/2004 |
| WO | 2006042838 A1 | 4/2006 |

OTHER PUBLICATIONS

P.-A. Auroux, et al., Miniaturised Nucleic Acid Analysis, The Journal Is the Royal Society of Chemistry 2004, Lab Chip, 2004, 4, pp. 534-546.

Robin Hui Liu, et al., Self-Contained, Fully Integrated Biochip for Sample Prpearation, Polymerase Chain Reaction Amplification, and DNA Microarray Detection, Analytical Chemistry, vol. 76, No. 7, Apr. 1, 2004, pp. 1824-1831.

Eric T. Lagally, et al., Fully Integrated PCR-Capillary Electrophoresis Microsystem for DNA Analysis, This Journal Is the Royal Society of Chemistry 2001, Lab on a Chip, 2001, 1, pp. 102-107.

W.J. Benett, et al., Handheld Advanced Nucleic Acid Analyzer, Biochemical and Biomolecular Sensing, Robert A. Liberman, Editor, Proceedings of SPIE, vol. 4200 (2000), pp. 55-63.

Magnetic Shielding (retreived on Feb. 11, 2014 from the Internet: http://www.magneticshielding.com/magnetic-shielding-faq.html).

MuMetal (retreived on Feb. 11, 2014 from the internet: http://metals.about.com/library/bldef-Mu-Metal.htm).

Nickel Alloys.net (retreived on Feb. 11, 2014 from the internet: http://www.nickel-alloys.net/nickelalloys.html).

Jesse S. Buch, Christopher Kimball, Frederick Rosenberger, W. Edward Highsmith, Jr., Don L. De Voe and Cheng S. Lee; DNA Mutation Detection in a Polymer Microfluidic Network Using Temperature Gradient Gel Electrophoresis; Analytical Chemistry, vol. 76, No. 4, Feb. 4, 2004; pp. 874-881.

Thomas C. Tisone, Dispensing Systems for Miniaturized Diagnostics; IVD Technology Magazine, Originally Publihsed May 1998; Retrieved on Sep. 28, 2016 From the Internet: http://www.bioon.com/biochip/general/011-2.html.

* cited by examiner

SYSTEM FOR OPERATING A SYSTEM FOR THE INTEGRATED AND AUTOMATED ANALYSIS OF DNA OR PROTEIN

CROSS REFERENCE TO RELATED APPLICATION

This application is a continuation of commonly owned, co-pending U.S. patent application Ser. No. 11/920,978, filed Jul. 23, 2009, which is a § 371 of PCT/EP2006/062499 filed May 22, 2006 and claims 35 USC § 119 priority of German Patent Application DE 10 2005 024 610.9 filed May 25, 2005.

BACKGROUND OF THE INVENTION

Field of the Invention

At least one embodiment generally relates to a system for the integrated and automated analysis of DNA or protein, for example one comprising a single-use cartridge (card), an evaluation device and a device for signal recording and processing. In particular, at least one embodiment of the invention generally relates to a control device as part of the evaluation device for the fully automatic processing and evaluation of molecular diagnostic analyses with disposable cartridges ("lab-on-a-chip") and also known as a biochip; see, commonly owned U.S. Patent Application Publication 2007/01411553). In addition, at least one embodiment of the invention also generally relates to a method for operating the type of system.

Description of Related Art

The significance of decentralized analysis devices ("point of care", "near patient testing") in molecular diagnostics or general medical technology is increasing. In addition, fast tests are becoming more and more important in the areas of foodstuff monitoring and environmental protection.

The general literature, but also especially the patent literature includes a large number of publications on the aforementioned topic: International Patent Application Publications WO 02/072 262 A1 and WO 02/073 153 A1 (which corresponds to U.S. Patent Application Publication 2005/0031490) disclose systems for application in biomedical technology in which samples taken in a decentralized manner are evaluated in a decentralized manner by means of an optionally mobile read-out device. The samples, in particular, are in this case collected in a single-use cartridge formed like a check card ("card").

Such a cartridge for application in the DNA analysis of whole blood samples is disclosed in detail in International Patent Application Publication WO 2006/042 838 A1 and corresponding U.S. Pat. No. 7,851,227, not previously published. In this case, the following features of the cartridge are regarded as essential for automatically carrying out all the measures required for process analysis from individual partial processes in the cartridge:

the cartridge contains a system of microchannels and/or microcavities for a microfluidic process technology, the microchannels or the microcavities have predetermined geometrical structures for receiving reagents, wherein the reagents are stored in a storage-stable form at specific locations in the microchannels or the microcavities of the cartridge, means are present for providing the dry-stored reagents for the respective partial process in a suitable form, in particular as a liquid reagent.

Reference is expressly made to the disclosure of these features in the above earlier application.

Furthermore, U.S. Patent Application Publications 2002/0179444 A1 and 2003/0148530 A1 disclose individual solutions for a blood diagnosis method and the associated signal processing. Specific problem solutions for the realization of the system of the type mentioned in the introduction comprising the previously described card and associated suitable means for evaluation are described in earlier applications in the name of the applicant that have not yet been published.

SUMMARY OF THE INVENTION

At least one embodiment of the invention is directed to a system which meets practical requirements in particular with regard to the evaluation device. At least one embodiment is directed to an associated control method for evaluation in the case of a system comprising cartridge and evaluation device. In the case of at least one embodiment, the following requirements are made of the evaluation device:

low price small structural design simple operating control ("one button" operation)

rapid performance of the analysis integrated microfluidics safety against contamination, i.e., avoidance of instances of soiling and infections-high operational reliability capability of communication with data processing systems.

No practically suitable solution has been disclosed hitherto for the fully automatic nucleic acid analysis from taking the sample (e.g., blood) to displaying the result, in particular including cell disruption, PCR and detection. Since the equipment currently proposed for biochemical analysis does not yet meet all the practical requirements, at least one embodiment of the invention improves the system so as to allow a maximally automated and reproducible evaluation. In particular, the intention here is to ensure that the result is displayed directly on a display or the data are forwarded into a computer system. The intention is to specify, in at least one embodiment, a suitable operating method for this purpose.

The operating method of at least one embodiment for carrying out an evaluation of a sample in a single-use cartridge with the aid of the control device in a system. Especially the realizations for carrying out a DNA analysis, and also in particular an SNP analysis, or alternatively a protein analysis, are contained in further embodiments of the method.

The basis of at least one embodiment of the invention, therefore, is an improved concept by comparison with the prior art: a device construction realized in accordance with this concept is designed according to at least one embodiment of the invention for the fully automatic processing and evaluation of molecular diagnostic analyses with disposable cartridges (lab-on-a-chip), in particular for the control and read-out of analysis processes within cartridges in the form of modified check cards.

In the case of at least one embodiment of the invention, the control device has the following features, in particular:

a cartridge receptacle for receiving, locking, unlocking and releasing the cartridge, a device for correctly positioning the cartridge in the reader, sensors for identifying the cartridge, in particular a correct cartridge, e.g., limit switches, barcode, a water reservoir for diluting the sample, dissolving dry reagents of the cartridge, carrying out flushing operations, wherein fluidic contact can be made with the water reservoir by way of a septum being pierced by a pointed hollow needle, a sterile filter ventilation valve for ventilating the water reservoir when water is drawn, a power supply unit, a pump for conveying extremely small quantities of liquid, for example in the microliters range, means for distributing water via valves, e.g., water-carrying solenoid valves, a pressure sensor in the water feed for monitoring fluidic operations, at least one interface for feeding water into the cartridge, sensors for identifying the filling of throughflow channels on the cartridge, e.g., capacitive sensors with electrodes above and below the cartridge, a device for closing off and opening venting openings of the cartridge, e.g., air-carrying solenoid valves, a device for closing off and opening chambers, in particular the PCR chamber, on the cartridge, e.g., plungers pressing onto a film, a combination comprising a magnetic bead collector and a thermostatic regulation device for capturing magnetic beads and for carrying out thermocycling processes for the PCR, a sandwich arrangement of two abovementioned devices for rapid thermocycling, a device for ensuring optimum heat transfer between the thermostatic regulation device and cartridge, e.g., by way of a contact pressure defined by way of springs, a device for making electrical contact with an electrical detection module, e.g., contact pins, an integrated thermostatic regulation for the detection module, control, measuring and regulating electronics for all the functions, a microcontroller for control and data acquisition, and a display for representing the analysis results.

In the associated method for operating the control and read-out device for the evaluation of a cartridge filled with a sample, the following method steps are carried out specifically for a DNA analysis:

the cartridge receptacle is opened and the pump draws water from the reservoir given a suitable valve position, the control device indicates readiness for operation, a user inserts the cartridge with a sample, e.g., blood, the analysis is started by a "one button" action or automatically, e.g., by way of a cartridge limit switch, given a suitable valve position, water is pumped into the cartridge via a water port in order to wash out excess sample material, the venting valves are actuated in a suitable manner in order to allow or prevent the filling of cartridge channels by way of permitting or avoiding venting, as a result of the inflow of water, the sample is diluted and pumped into the cell disruption channel, wherein dry reagents are dissolved, a residence time ensues for cell disruption, wherein liberated DNA binds to magnetic beads, nearly at the same time two ELISA reagent channels are filled, wherein dry ELISA reagents (enzyme label and substrate) are dissolved, the content of the cell disruption channel is flushed by further pumping of water through the PCR chamber, wherein the magnetic beads with DNA are held back by a magnetic field, the remainder is flushed into a waste channel, the valves of the PCR chamber are closed off, the thermocycling is started, wherein dry PCR reagents are dissolved, a predetermined number of thermocycles are carried out at defined temperatures (PCR), the valves of the PCR chamber are opened after conclusion of the PCR, given a suitable valve position, water is pumped into the cartridge via a further water port and the PCR product is flushed from the PCR chamber into a detection chamber, the detection chamber is thermostatically regulated, wherein hybridization of the DNA with catcher molecules takes place, air possibly present between the PCR product and the dissolved ELISA reagents is pumped into a waste channel by suitable setting of water port and venting valves, the dissolved enzyme label is pumped via the detection chamber into a further waste channel by suitable setting of water port and venting valves, the dissolved substrate is pumped via the detection chamber into a further waste channel by suitable setting of water port and venting valves, the electrical detection is started, e.g., an SNP analysis is carried out by recording melting curves.

As an alternative to the above method sequence, a protein analysis is also possible, wherein no cell disruption and no PCR are necessary. In this case, the proteins sought are isolated from the sample by way of magnetic beads and detected in the detection chamber. Haptens can be detected analogously.

An analysis process integrated throughout is carried out, then, by the method according to an embodiment of the invention. This is understood to be a fully automated method sequence without manual intervention. After the introduction of the cartridge with the sample into the control device, the sample treatment and analysis process proceeds automatically until the actual detection of the substances sought. This has the advantage, in particular, of high reproducibility and a low error rate.

What is particularly advantageous in the system according to at least one embodiment of the invention is that the control device can be embodied in compact fashion and has both internal fluidic interfaces and electrical interfaces. Interfaces for linking to external computer systems are additionally present. These may be serial and/or wireless interfaces, for example. In an example embodiment, the control device comprises a connection possibility for a commercially available PDA. This enables a display to be integrated into the control device in a simple manner. In a particularly preferred example embodiment, a display and operating unit is fixedly integrated into the control device.

With the system according to at least one embodiment of the invention, a considerable advance is achieved compared with the previously proposed devices. It is now possible, for example, for the measured data to be directly displayed or forwarded for evaluation.

Further details and advantages of the application are explained on the basis of the example embodiment described below in association with the accompanying drawings, in which:

DETAILED DESCRIPTION OF THE INVENTION

An analysis device is described below as one example embodiment of the invention. The analysis device is divided into a control device and a cartridge. Whereas the cartridge is, for example, present as a disposable article on which the actual analysis process proceeds, the control device is reusable and serves for controlling the analysis process. The cartridge contains only passive components; the entire control proceeds from the control device.

Figure 1:
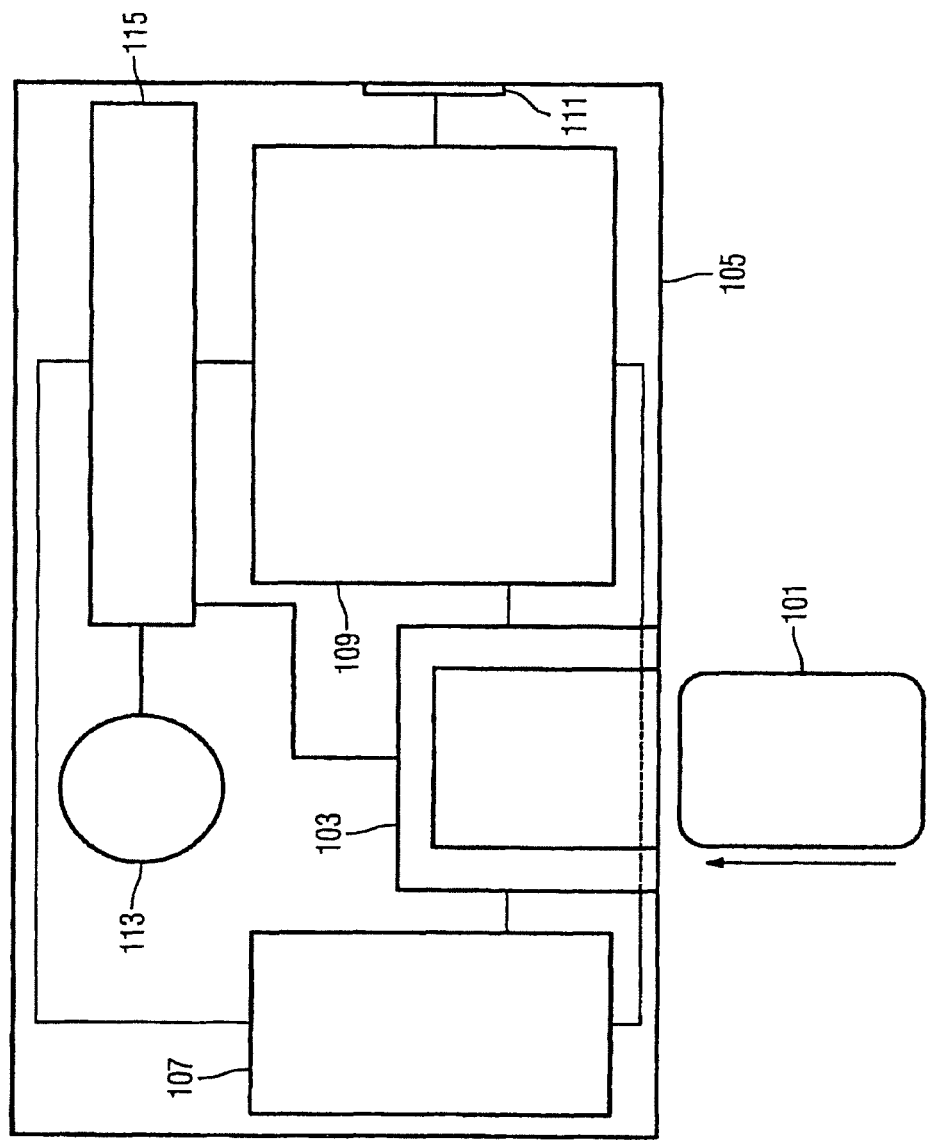
FIG. 1 shows a schematic overview diagram of an analysis device.

FIG. 1 shows the construction of the analysis device. It includes a cartridge 101, which can be inserted into a cartridge receptacle 103 of a control device 105. The cartridge receptacle 103 is connected to a power supply unit 107, which supplies the receptacle with power. For the transmission of data of the analysis process, the cartridge receptacle 103 is additionally connected to an electronic unit 109. The data can be output from the electronic unit 109 via an interface 111.

The interface 111 is formed as an RS232 interface, for example. The electronic unit 109 is connected to the power supply unit 107 for its power supply.

In order to carry out the analysis process, water is required in the cartridge. This water is stored in a supply container 113. The supply container 113 is a commercially available bottle containing sterile, distilled water, for example, which is closed off by a septum. A corresponding receptacle for the bottle in the control device is provided with a cannula which pierces the septum when the bottle is inserted. As a result, the water becomes accessible and it can be drawn from the bottle via a connected pump 115. The pump 115 can take up a defined quantity of water and pump it into the cartridge receptacle 103 via a connection. The water passes into the cartridge 101 via the cartridge receptacle 103 and is available in the analysis process. The pump 115 is connected to the power supply unit 107 for its power supply.

Figure 2:
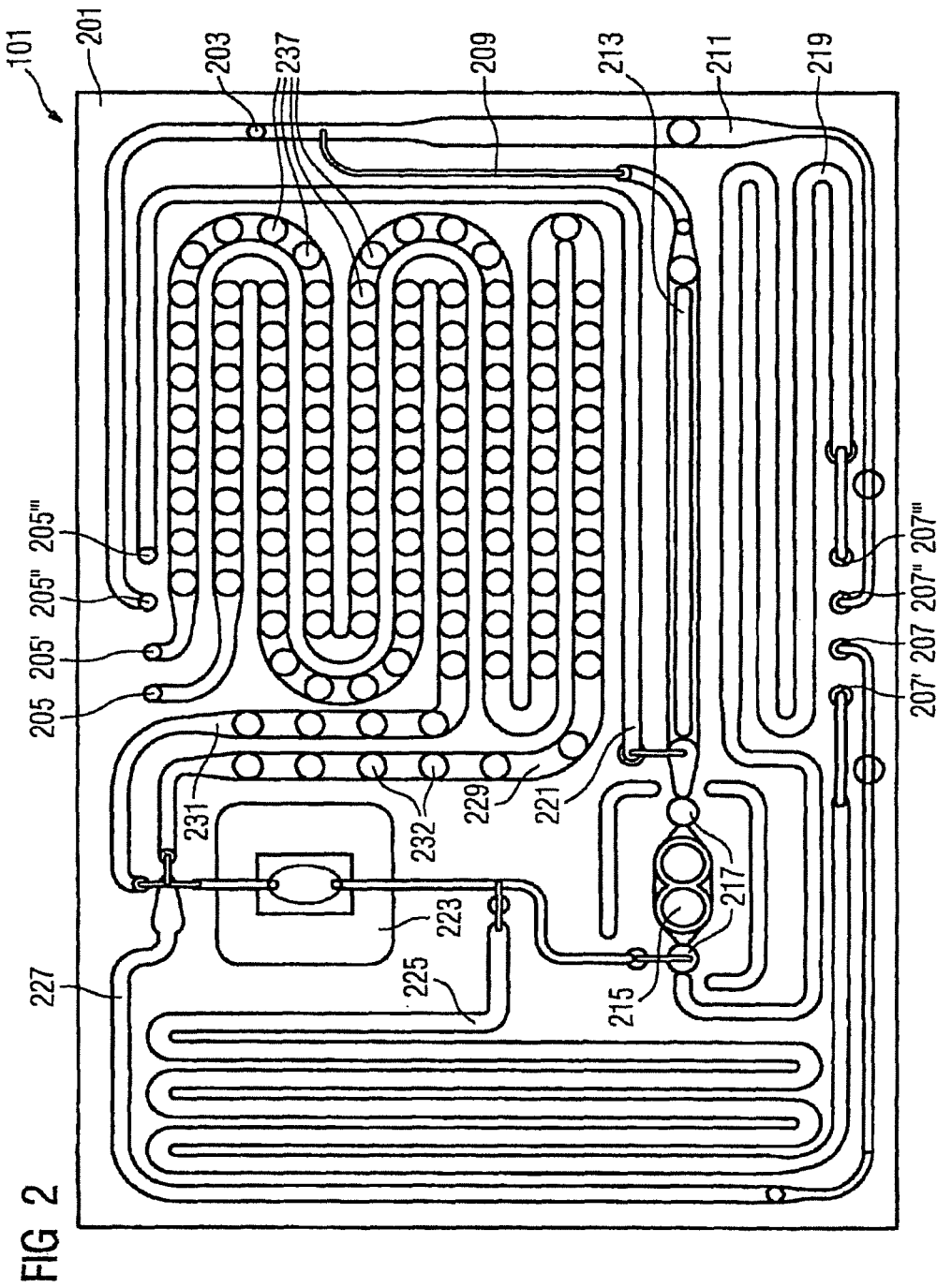
FIG. 2 shows a schematic overview diagram of a cartridge.

FIG. 2 schematically illustrates the cartridge 101, which has already been disclosed in detail in International Patent Application Publication WO 2006/042 838 A1 and corresponding U.S. Pat. No. 7,851,227, not previously published, which disclosure is also subject matter of the present patent application, wherein the entire contents thereof is hereby incorporated herein by reference.

The cartridge 101 is present in the form of a plastic card 201 of the size of a check card and comprises a number of channels. Via a sample port 203, a sample can be pipetted into the cartridge 101. Water can be introduced into the cartridge 101 via four water ports 205, 205', 205" and 205'". The cartridge 101 is additionally provided with four venting ports 207, 207', 207" and 207'", through which air can escape when the channels are filled. A metering section 209 comprises a volume of 1l and services for tapping of this quantity from the sample that has been pipetted in. A sample waste channel 211 serves for receiving the rest of the sample. The venting port 207'" lies at the end of the sample waste channel 211. The metering section 209 is adjoined by a cell disruption channel 213, in which reagents for the cell disruption are stored in dry form. It is only as a result of the introduction of the sample in diluted form that the reagents are dissolved and cell disruption takes place. As a result of the cell disruption, DNA contained in the cells is liberated, said DNA binding to magnetic beads likewise present in the cell disruption channel 213.

The cell disruption channel 213 is connected to a PCR chamber 215, in which a PCR can be carried out. The PCR chamber 215 can be closed off by way of two valves 217. The required reagents are situated in the PCR chamber 215 likewise in dry form. Arranged downstream of the PCR chamber 215 is a PCR waste channel 219 connected to the venting port 207". A water channel 221 connected to the water port 205" leads in at one end of the cell disruption channel 213. The PCR chamber 215 is connected to a detection chamber 223, in which the DNA can be detected by means of a sensor array. The detection chamber 223 is connected to two waste channels 225 and 227 ending in the ventilation ports 207' and 207, respectively. In addition, the detection chamber 223 is connected to two ELISA reagent channels 229 and 231 (ELISA: enzyme linked immuno sorbent assay), which, for their part, are connected to the water ports 205' and 205, respectively. ELISA reagents 232 are stored in dry form in the ELISA reagent channels 229 and 231, and after being dissolved in water can be flushed into the detection chamber 223.

Figure 3:
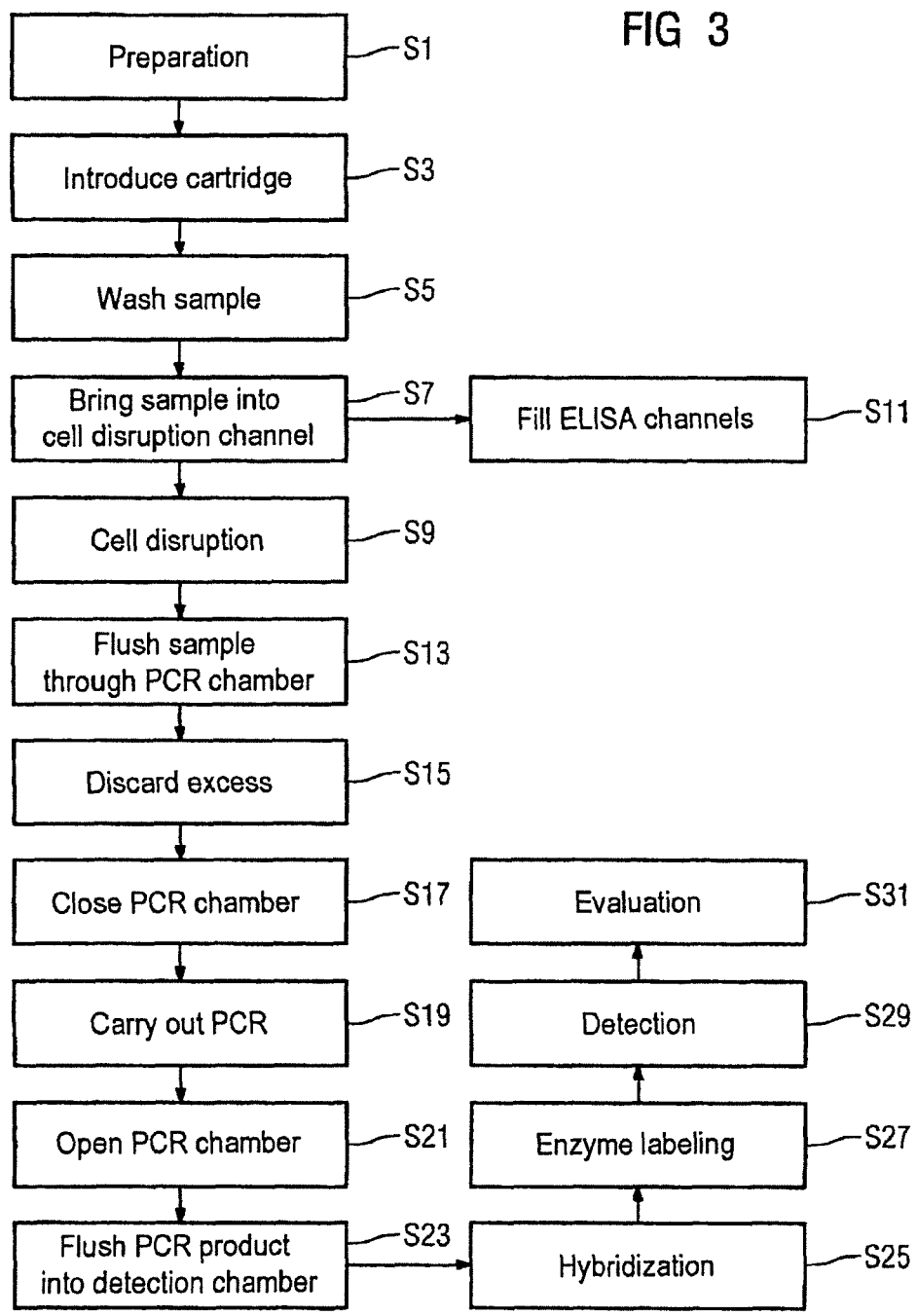
FIG. 3 shows a schematic flowchart of an analysis method.

FIG. 3 shows a schematic flowchart of an analysis process. In a first method step S1, the cartridge is prepared. This involves pipetting the sample into the cartridge and possibly providing water in the control device. As it is pipetted in, the sample accumulates in the sample waste channel 211 of the cartridge (referring to FIG. 2), the metering section 209 likewise filling up in the process. In a second method step S3, the cartridge is introduced into the control device. As a result of the introduction of the cartridge, valves situated in the read-out device are connected to the water ports 205 to 205'" and the venting ports 207 to 207'", such that water can be introduced into the cartridge and air can escape. Moreover, a switch in the read-out device is actuated, whereupon the analysis process starts automatically.

In this case it is ensured by way of functional elements known per se that the cartridge is in the correct position and has the correct orientation. Moreover, the fact of whether the cartridge is one which is suitable for the control device is identified. At the beginning of the analysis process within the cartridge 101, the water channel 221 is filled with water, the water channel 221 likewise being vented via the PCR waste channel 219. This simplifies the method sequence since the air present in the water channel 221 could not escape in the further sequence.

In a third method step S5, water is pumped into the water port 205'", such that that portion of the sample which is situated in the metering section 209 is isolated. The venting port 207', which is otherwise closed off by the valve, is opened for this purpose. As soon as the sample waste channel 211 has been filled, the venting port 207' is closed off again in a fourth method step S7. The filling level of the sample waste channel 211 is measured by way of filling level sensors arranged in the control device. The functioning is explained with reference to FIGS. 6 and 7.

As a result of the venting port 207' being closed off, pressure starts to build up as water continues to be pumped in, such that that portion of the sample which is situated in the metering section 209 is flushed into the cell disruption channel 213. The valve assigned to the venting port 207" in the control device is opened for this purpose. The sample is diluted with water. As a result of the introduction of the diluted sample, the dry reagents in the cell disruption channel 213 are dissolved whereupon cell disruption takes place in a fifth method step S9. DNA situated in the cells of the sample is liberated in this case. The liberated DNA binds to magnetic beads stored in the cell disruption channel 213.

At the same time as the cell disruption, in a sixth method step S11, the ELISA reagent channels 229 and 231 are filled with water. The valves assigned to the venting ports 207' and 207 in the control device are opened for this purpose. The filling level of the ELISA reagent channels 229 and 231 is measured by filling level sensors arranged in the control device.

After the cell disruption has been concluded, in a seventh method step S13, the diluted sample with the magnetic bead-DNA complexes is flushed through the PCR chamber 215. For this purpose, as already previously, water is pumped through the water port 205' and the venting port 207" is opened. In the control device, there is a magnet arranged above the PCR chamber 215, the magnetic bead-DNA complexes being held back in the PCR chamber 215 by said magnet. The remainder of the diluted sample is flushed into the PCR waste channel 219. In an eighth method step S15, water is again pumped through the PCR chamber 215, thereby cleaning the magnetic bead-DNA complexes.

In a ninth method step S17, the valves 217 of the PCR chamber 215 are closed. In a tenth method step S19, the DNA of the magnetic bead-DNA complexes is replicated by a PCR. For this purpose, corresponding reagents are situated in the PCR chamber 215 in dry form, said reagents being dissolved by the addition of water. In order to manipulate the temperature in the PCR chamber 215, two Peltier units are situated in the control device. After the conclusion of the PCR, in an eleventh method step S21, the valves 217 of the PCR chamber 215 are opened. In a twelfth method step S23, water is pumped into the channel 221 via the water port 205", such that the water previously situated in the channel 221 is flushed into the PCR chamber 215. The channel 221 contains dry stored salts which are thus added to the PCR product, that is to say the replicated DNA. At the same time, the replicated DNA is flushed from the PCR chamber 215 into the detection chamber 223. In this case, the venting ports 207" and 207' are closed, and the venting port 207 is open.

In a thirteenth method step S25, a hybridization between the PCR product and capture molecules arranged in the detection chamber 223 takes place in the detection chamber 223. In order to support the hybridization, the temperature in the detection chamber 215 is set in a defined manner by way of a Peltier element arranged in the control device. In a fourteenth method step S27, a label enzyme (e.g., streptavidin alkaline phosphatase, streptavidin esterase or oligonucleotide-coupled esterase) linked to a coupling molecule is pumped from the ELISA reagent channel 231 through the detection chamber. For this purpose, water is pumped through the water port 205 and the venting port 207' is opened. The DNA linked to the catcher molecules is marked by the label enzyme. In a fifteenth method step S29, a dissolved enzyme substrate is pumped from the ELISA reagent channel 229 through the detection chamber 215. Both enzyme label and enzyme substrate channel are vented before the flooding of the detection chamber 231 via the channel 227 in order to prevent air from being entrained into the detection chamber 223. By virtue of the substrate, a so-called redox cycling process occurs in the detection chamber, and the bound DNA can be detected by said process. Evaluation of the measurement data correspondingly takes place in a sixteenth method step S31.

Figure 4:
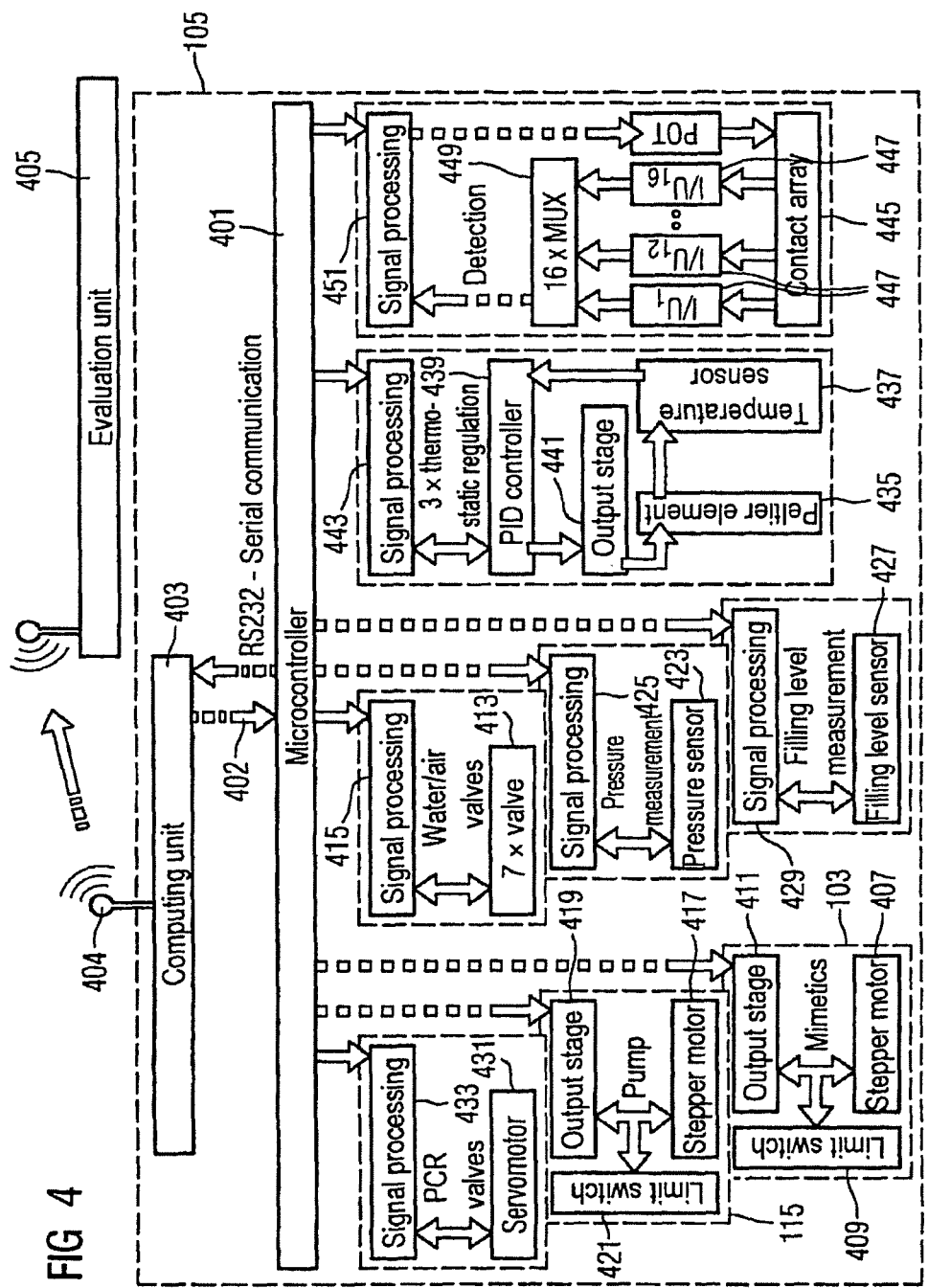
FIG. 4 shows a schematic overview diagram of the functional units of the control device.

FIG. 4 illustrates the central components of the control device 105 in a block diagram. A microcontroller 401 serves as central controller of the entire analysis process, said microcontroller being connected to a computing unit 403 via a serial RS232 interface 402. Said computing unit 403 is a commercially available PDA, for example, and serves for recording measurement data from the analysis process. The computing unit 403 is equipped with a radio module 404, via which the measurement data can be transmitted to an evaluation unit 405. The radio module 404 communicates with the evaluation server 405 for example by infrared, Bluetooth or WLAN.

The microcontroller 401 controls all the components of the control device 105 which are involved in the analysis process. The cartridge receptacle 103 comprises a stepper motor 407, which moves a part of the cartridge receptacle 103 upon insertion of the cartridge, such that the cartridge is correctly received. The Peltier elements are brought into position in this case. A limit switch 409 interrupts the process when the cartridge has been completely introduced. As a result of the introduction process, the water ports and the venting ports are connected to corresponding channels in the control device. Valves 413 controlled by the microcontroller 401 are arranged in the channels. A signal processing unit 415 serves for communicating the control signals. The arrangement and functioning of the channels and valves are explained with reference to FIG. 5.

For the movement of the water in the channels, the pump 115 is controlled by the microcontroller 401. Its piston is moved by a stepper motor 417, which is in turn controlled by means of an output stage 419 and a limit switch 421. The pressure in the pump 115 is measured by means of a pressure sensor 423 and read out by the microcontroller 401 via a signal processing unit 425.

The movement of the water in the cartridge is monitored by means of filling level sensors 427, which are read by the microcontroller 401 via a signal processing unit 429.

The valves of the PCR chamber are controlled via a servomotor 431 and a signal processing unit 433. Three Peltier elements 435 and temperature sensors 437, which are controlled and read via a PID controller 439 and an output stage 441, serve for the thermostatic regulation of the PCR chamber and the detection chamber. The PID controller 439 is controlled by the microcontroller 401 via a signal processing unit 443.

The signals generated by the redox cycling on the sensor array are measured via a contact-making module 445 and forwarded to a signal processing unit 451 via read-out circuits 447 and a multiplexer 449. The signal processing unit 451 is connected to the microcontroller. The necessary control voltages, such as e.g., a reference voltage and a counter-voltage of a potentiostat, are fed to the sensor array via the contact-making module 445. The sensor array is embodied as a CMOS sensor chip, for example. In this case, the contact-making module 445 advantageously has the arrangement as in a commercially available smart card reader.

Figure 5:
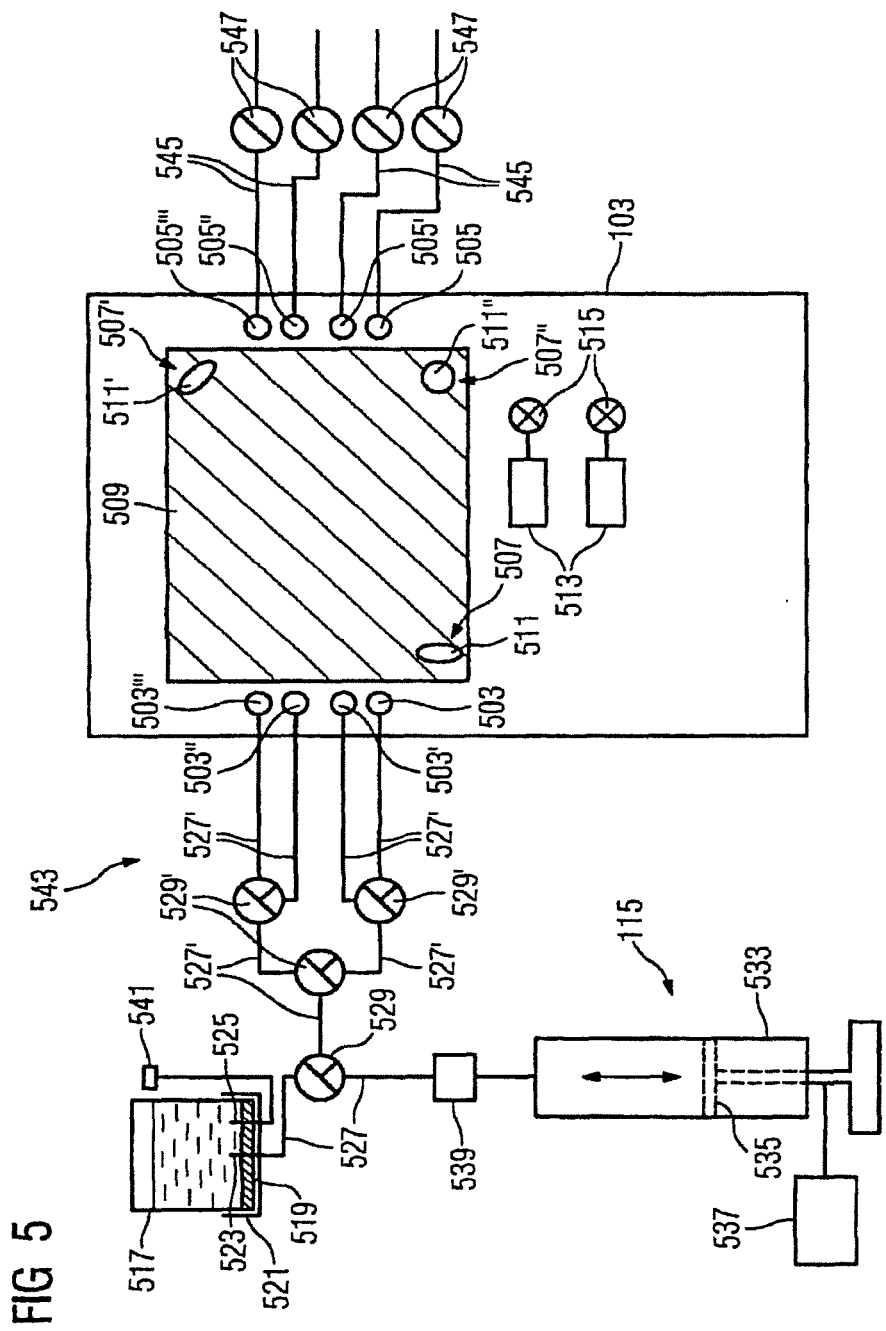
FIG. 5 shows a schematic overview diagram of the fluidic components of the control device.

FIG. 5 illustrates a schematic overview diagram of the fluidic components of the control device. The cartridge receptacle 103 includes four water ports 503, 503', 503" and 503''', which are connected to the water ports of the cartridge when the latter has been inserted. Four venting ports 505, 505', 505" and 505' are likewise provided, which are connected to the corresponding venting ports of the cartridge. The cartridge receptacle 103 furthermore includes three filling level sensors 507, 507' and 507", the functioning of which is explained with reference to FIGS. 6 and 7. They operate capacitively and comprise two capacitor plates. In order to ensure a simple construction of the cartridge receptacle 103, one capacitor plate 509 is formed in large-area fashion and is used jointly for all the filling level sensors 507, 507' and 507". The other capacitor plates 511, 511' and 511" are correspondingly embodied separately.

The filling level sensors 507 and 507' are designed in each case for monitoring two channels of the cartridge and are arranged at corresponding locations of the cartridge receptacle 103. The filling level sensor 507 serves for monitoring the two ELISA reagent channels 229 and 231, while the filling level sensor 507' monitors the sample waste channel 211 and the PCR waste channel 219. The filling level sensor 507" serves for monitoring the waste channel 227.

Two motors 513 for controlling two actuators 515 are additionally arranged in the cartridge receptacle 103. The actuators 515 serve for opening and closing the valves of the PCR chamber on the cartridge.

The water required for the analysis process comes from a commercially available bottle 517, which is closed off by a septum 519. The bottle 517 is held by a receptacle 521 of the control device, two cannulas 523 and 525 being arranged in said receptacle. When the bottle 517 is introduced into the receptacle 521, the septum 519 is pierced by the two cannulas 523 and 525 and the water in the bottle 517 is made accessible. The cannula 523 is connected to a pump 115 via a line 527 and a three-way valve 529. By means of the pump 115, a volume of water that can be set in a defined manner can be drawn from the bottle 517. The pump 115 comprises a hollow cylinder 533 with a movable piston 535. The piston 535 can be moved in a defined manner by means of a stepper motor 537. A pressure sensor 539 is arranged in the line 527, and the pressure in the line 527 can be determined by way of the pressure sensor.

The cannula 525 serves for ventilating the bottle, since a negative pressure would otherwise arise when water is drawn. The cannula is connected to a sterile filter 541, via which air can pass into the bottle.

The three-way valve 529 can be connected to the four water ports 503, 503', 503" and 503''' via a line system 543. A plurality of lines 527' and three further three-way valves 529', by which the three-way valve 529 can be selectively connected to each of the water ports 503, 503', 503" and 503''', are provided for this purpose. Through suitable switching of the three-way valves 529', the water can thus be pumped from the hollow cylinder 533 into one of the water ports 503, 503', 503" or 503'". The pressure occurring in the line system 543 and the line 527 is detected by the pressure sensor 539 in this case.

The air present in the channels of the cartridge before the start of the analysis process must be able to pass out of the cartridge as the latter is filled with water. The four ventilating ports 505, 505', 505" and 505''' are provided for this purpose in the cartridge receptacle. They are connected via lines 545 to two-way valves 547, which can be optionally closed or open. When water is introduced into one of the channels, the corresponding one of the valves 547 is opened, such that air can escape from the cartridge.

Figure 6:
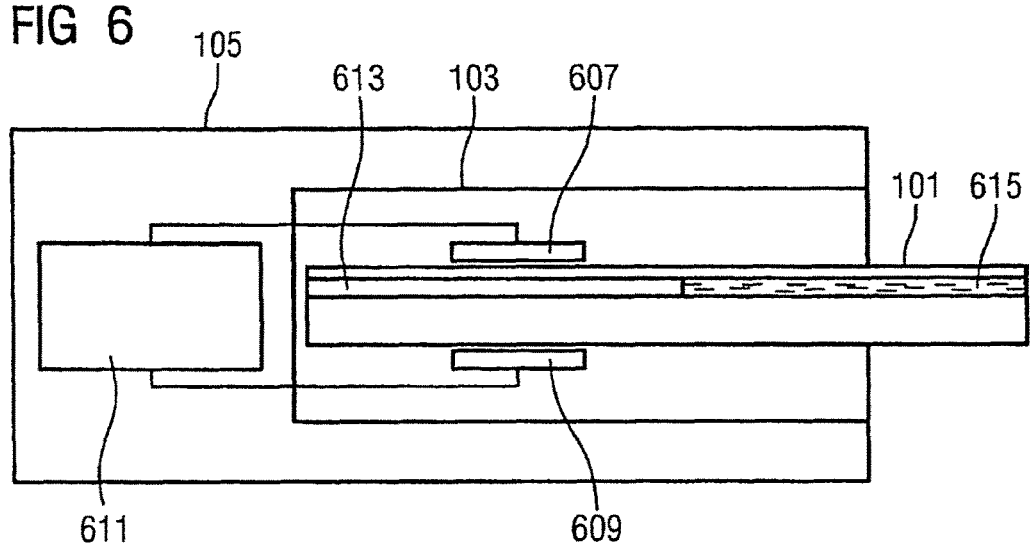
FIG. 6 and FIG. 7 show schematic illustrations of a measuring device for a filling level.
Figure 7:
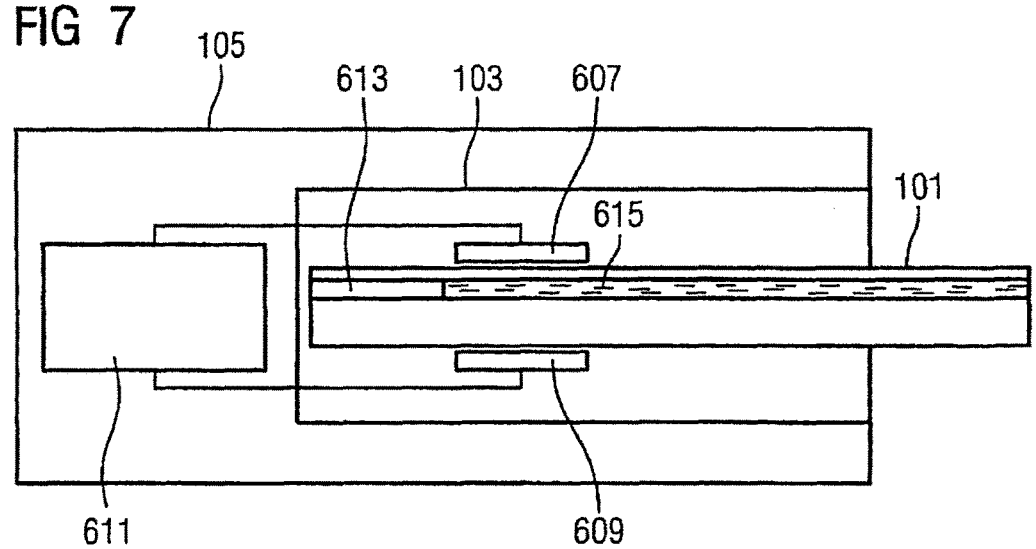

FIGS. 6 and 7 show the functioning of the filling level sensors. FIG. 6 illustrates the control device 105 in a sectional view. A cartridge 101 has been introduced into the cartridge receptacle 103. In the cartridge receptacle 103, two capacitor plates 607 and 609 are arranged above and below the cartridge 101. The capacitor plates 607 and 609 are connected to a measuring unit 611, by which the capacitance of the capacitor formed by the capacitor plates 607 and 609 can be determined.

In FIG. 6, a channel 613 shaped within the cartridge 101 is partly filled with water 615. In the illustration in FIG. 7, the channel 613 is filled to an extent such that there is water 615' between the capacitor plates 607 and 609. As a result, the capacitance of the capacitor is altered in comparison with the state illustrated in FIG. 6. The change is determined by means of the measuring unit 611 and the liquid level in the channel is determined in this way.

Figure 8:
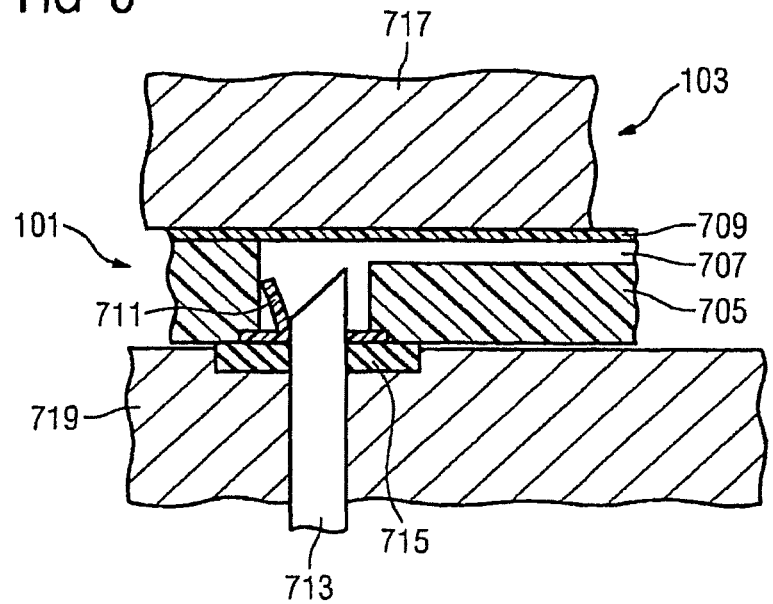
FIG. 8 shows a schematic illustration of a fluidic interface between the cartridge and the control device.

FIG. 8 shows a section through a part of the cartridge receptacle 103 with cartridge 101 inserted. The contact-making between the water ports of the control device 103 and the cartridge 101 is shown. A channel 707 is milled in a plastic body 705 of the cartridge 101. The channel 707 is covered by way of an adhesive film 709, the adhesive film 709 being adhesively bonded onto the plastic body 705. The adhesive film 709 is commercially available and compatible with all the processes that proceed in the cartridge 101. A further adhesive film 711 is fixed to the water port of the cartridge 101. The further adhesive film can be pierced by a hollow needle 713 arranged in the cartridge receptacle 103 and the fluidic contact between the cartridge receptacle 103 and the cartridge 101 can thus be established. A seal 715 that prevents liquids from escaping is arranged in the cartridge receptacle 103. the seal 715 is preferably composed of a biochemically compatible silicone material in order to avoid contamination of the water ports.

Before the cartridge 101 is introduced into the cartridge receptacle 103, an upper part 717 and a lower part 719 of the cartridge receptacle 103 are further away from one another than illustrated in FIG. 8. This enables the cartridge 101 to be introduced in a convenient manner. As soon as the cartridge 101 has been completely introduced, the two parts 717 and 719 are brought together and the cartridge 101 is locked in the cartridge receptacle 103. At the same time, the adhesive film 711 is pierced by the hollow needle 713.

Figure 9:
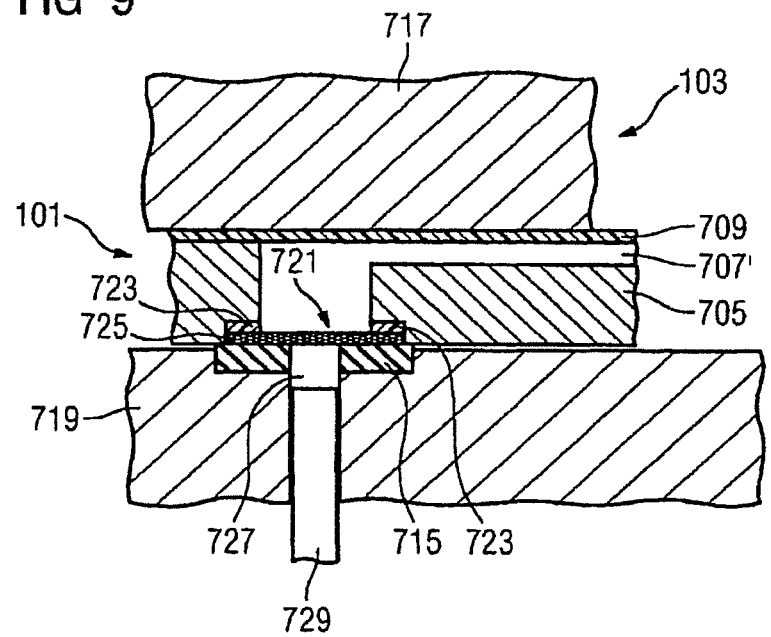
FIG. 9 shows a schematic illustration of a venting interface between the cartridge and the control device.

FIG. 9 shows a section through a part of the cartridge receptacle 103 with inserted cartridge 101 at one of the venting ports. In the cartridge 101, analogously to the illustration in FIG. 8, a channel 707' is milled into the plastic body 705, said channel being covered by the adhesive film 709. Around the venting port 721 of the cartridge 101, a depression is milled into the plastic body 705, an adhesive layer 723 being arranged in said depression. A Teflon membrane 725 is fixed on the adhesive layer 723. A seal 715 is arranged in the lower part 719 of the cartridge receptacle 103. A channel 727 is additionally provided, which runs through the seal 715 and is therefore in contact with the Teflon membrane 725. A hose 729 connected to the venting valves of the control device is arranged in the channel 727.

The Teflon membrane 725 ensures that no liquid can escape from the cartridge. This serves to avoid contamination of the control device, which is intended to be able to be used for a multiplicity of analysis processes. The sample introduced into the cartridge 101 generally contains infectious biomaterial which would contaminate the control device upon contact, and the control device would therefore have to be cleaned or replaced for carrying out further analysis processes. The Teflon membrane 725 is permeable to vapor and gas, but impermeable to liquids. By way of the pressure sensor 539 of the control device it is ensured that the pressure in the cartridge 101 does not become excessively high and the Teflon membrane 725 or the adhesive film 709 is not damaged or torn.

Figure 10:
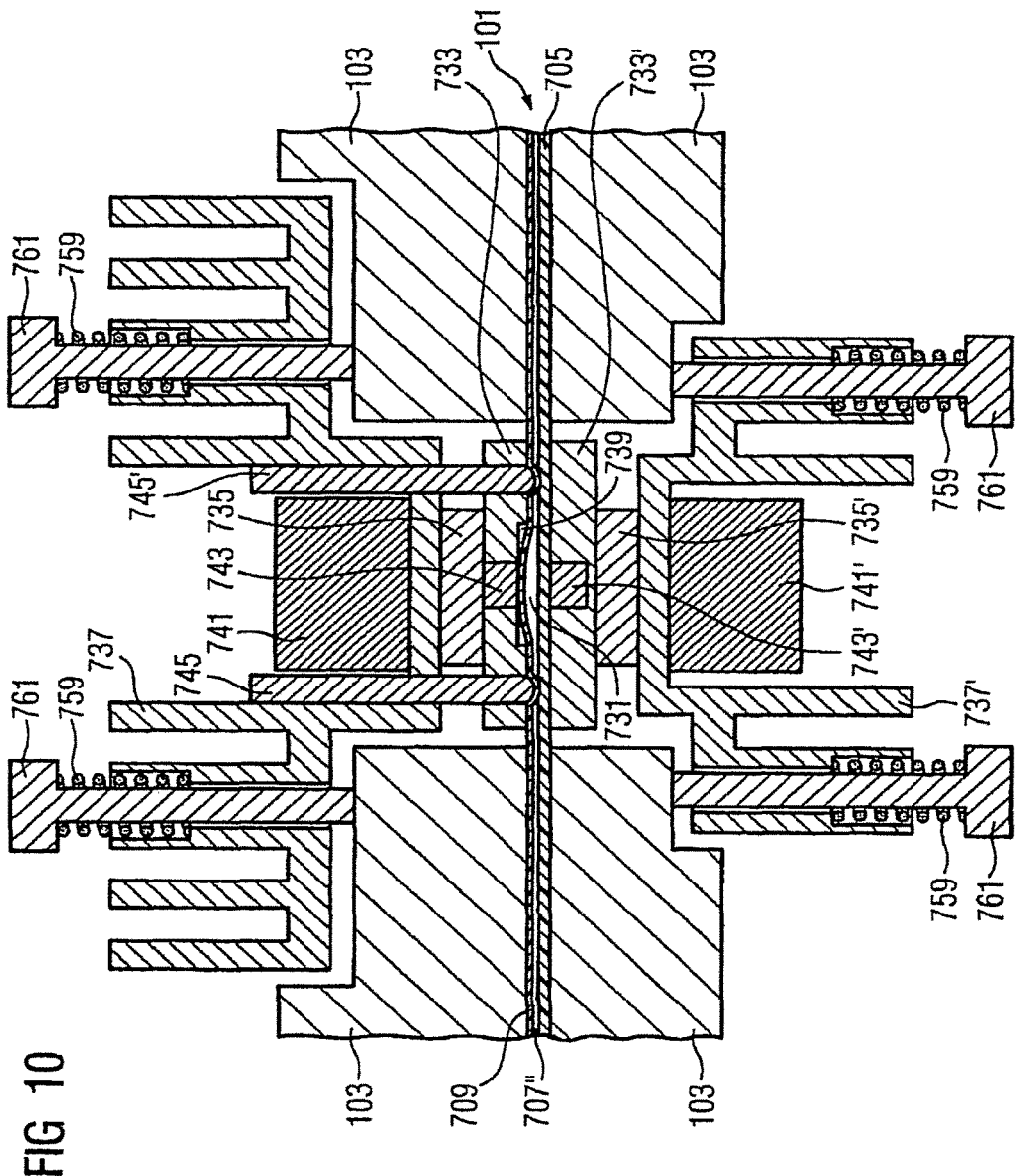
FIG. 10 shows a schematic illustration of a PCR chamber of the cartridge.

FIG. 10 illustrates a section through a part of the cartridge receptacle 103 with inserted cartridge 101. Analogously to FIGS. 8 and 9, a channel 707" is milled into the plastic body 705. The channel 707" has a widening serving as a PCR chamber 731. The channel 707" and the PCR chamber 731 are covered by the adhesive film 709.

In order to ensure rapid heat transfer for the thermocycling during the PCR, the PCR chamber 731 is kept as small as possible in a geometrical dimension (approximately 1 mm or volume <20 μl) and the heat transfers are realized in a "sandwich" thermostatically regulating arrangement such that only small liquid layers (a few 100 μm) have to be brought to thermal equilibrium. The PCR chamber 731 is preferably situated in a housing with plane-parallel outer surfaces (plastic body 705 with cutout and adhesive film 709).

In the cartridge receptacle 103, two thermal coupling plates 733 and 733', for example composed of aluminum, are arranged above and below the PCR chamber 731 of the cartridge 101. The two thermal coupling plates 733 and 733' are pressed against the adhesive film 709 and against the plastic body 705, respectively, and serve for transmitting thermal energy of two Peltier units 735 and 735' into the PCR chamber 731 when a PCR is carried out. The Peltier units 735 and 735' are in thermal contact with two heat sinks 737 and 737' which serve for dissipating heat during the cooling operations of the PCR cycles. They have a largest possible surface area in order to enable an efficient heat transfer to the ambient air, if appropriate with the aid of fans.

A cutout 739 is shaped in the thermal coupling plate 733. By virtue of the cutout 739, the adhesive film 709 can bulge out in the event of possible excess pressure, for example during a temperature increase in a PCR cycle.

Two permanent magnets 741 and 741' are arranged centrally above and respectively below the heat sinks 737 and 737'. The magnetic field generated by the permanent magnets 737 and 737' serves for holding back magnetic beads when the latter are flushed through the channel 707" into the PCR chamber 731. The DNA bound to the magnetic beads is thus held back for later replication by the PCR in the PCR chamber 731.

The field gradient generated by the two permanent magnets 741 and 741' is too small, however, to efficiently hold back the magnetic beads. In order nevertheless to obtain a high field gradient in the PCR chamber 731 along the throughflow direction of the liquid containing the magnetic beads, the thermally conductive but magnetically neutral thermal coupling plates 733 and 733' are equipped with small-volume bodies 743 and 743' (approximately 5 mm$^3$) composed of a material having a high relative permeability μ(r), in conjunction with still good thermal conductivity, preferably permalloy (Ni—Fe) or Mumetal (Ni/Fe/Cu/Mo).

The small-volume bodies 743 and 743' respectively form a magnetic core directly at the surfaces of the PCR chamber 731. The PCR chamber 731 is then situated directly between the magnetic cores. The magnetic cores are magnetized by the magnetic field of the permanent magnets 741 and 741'. The magnetic field lines are concentrated by way of the magnetic cores, whereby a high field gradient is generated.

In the field gradient arranged parallel to the outer walls of the PCR chamber 731 and flow direction of the solution containing magnetic beads, the magnetic beads are drawn in, detained and therefore concentrated.

The PCR chamber 731 can be closed up by way of two plungers 745 and 745'. The plungers 745 and 745' can be pressed against the adhesive film 709 by way of springs and cams that are not illustrated here, such that the PCR chamber 731 is closed off.

The heat sinks 737 and 737' are connected to screws 761 via springs 759. The screws 761 are screwed into the cartridge receptacle 103. The thermal coupling plates 733 and 733' connected to the heat sinks 737 and 737', respectively, are pressed against the adhesive film 709 and the plastic body 705, respectively, by the springs 759, such that good thermal contact arises. At the same time, thermal contact between the thermal coupling plates 733 and 733' and the cartridge receptacle 103 is avoided to the greatest possible extent.

Figure 11:
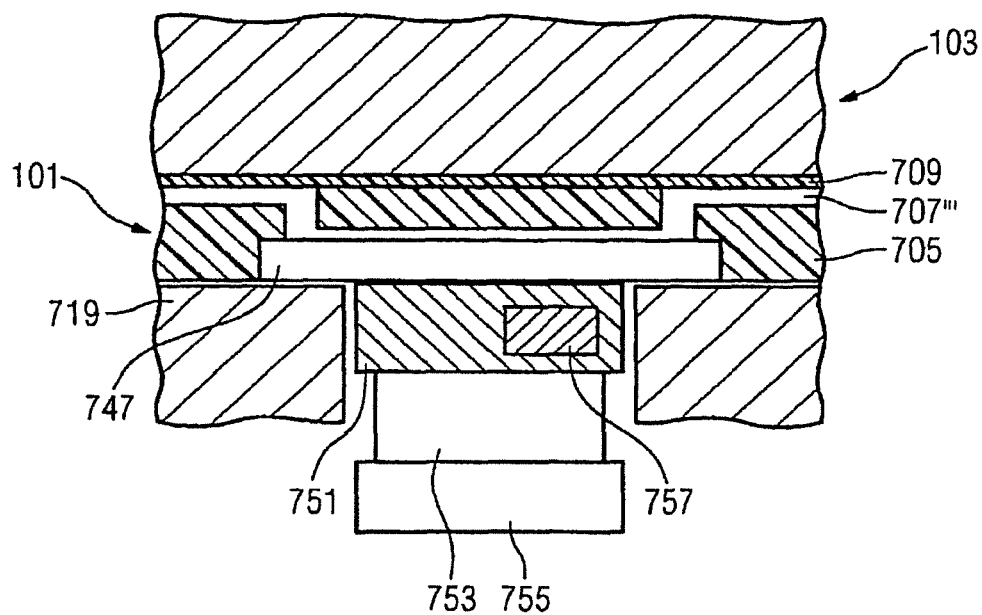
FIG. 11 shows a schematic illustration of a detection chamber of the cartridge.

FIG. 11 illustrates a section through a part of the cartridge receptacle 103 with inserted cartridge 101. A further channel 707''' is milled into the plastic body 705, said further channel being covered with the adhesive film 709. A chip module 747, by means of which the DNA contained in the sample can be detected, is arranged in the plastic body 705. By way of example, a redox cycling process for detecting the DNA can take place on the chip module 747.

In order to support the hybridization between the DNA and corresponding capture molecules that takes place at the surface of the chip module 747, the chip module 747 is thermally coupled to a Peltier element 753 via a thermal coupling plate 751. The Peltier element 753 is thermally coupled to a cooling unit 755. The temperature in the vicinity of the chip module 747 can be monitored by way of a temperature sensor 757 arranged in the thermal coupling plate 751. SNP analyses, for example, can thus be carried out by means of determining melting curves.

Outside the plane of the drawing, the unit formed from the thermal coupling plate 751, the Peltier element 753 and the cooling unit 755 is connected to the lower part 719 of the cartridge receptacle. In this case, the unit is mounted in resilient fashion, such that it is pressed against the cartridge 101 and a good thermal contact between the thermal coupling plate 751 and the chip module 747 is established.

Moreover, outside the plane of the drawing, sprung contact pins are provided within the lower part 719 of the cartridge receptacle 103, and tap off electrical signals of the chip module 747 for evaluation.

A practically suitable determination of DNA, proteins and also haptens is now possible with the described system including smart card for sample uptake and evaluation device with control device for sample processing and evaluation when the cartridge has been introduced into the evaluation device.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system for the integrated an automated analysis of DNA or protein, comprising:
   a cartridge to receive a sample to be analyzed, the cartridge containing a reagent for analysis of the sample;

a control device for controlling an analysis process, wherein the control device comprises:
a cartridge receptacle for receiving the cartridge;
means for moving a part of the cartridge receptacle upon insertion of the cartridge into the cartridge receptacle, such that the cartridge is correctly received in the cartridge receptacle;
a microcontroller for control and data acquisition; and
wherein the two parts of the cartridge receptacle are brought together as soon as the cartridge has been completely introduced in the cartridge receptacle,
wherein the control device comprises a thermostatic regulation device for carrying out at least one thermocycling process, wherein the thermostatic regulation device comprises two thermal coupling plates arranged so as to provide good thermal contact with the cartridge while avoiding thermal contact between the thermal coupling plates and the cartridge receptacle, and wherein the cartridge, in an inserted state, is situated between the thermal coupling plates and the thermal coupling plates are pressed against the cartridge such that the cartridge is held between the thermal coupling plates.

2. System according to claim 1, wherein the cartridge comprises a sample port, wherein the sample port is configured to enable the sample to be pipetted into the cartridge via the sample port.

3. System according to claim 1, wherein the cartridge is a single-use cartridge.

4. System according to claim 1, wherein the cartridge is in the form of a plastic card.

5. System according to claim 1, wherein the cartridge comprises a plurality of microfluidic channels.

6. System according to claim 5, wherein the control device comprises at least one valve arranged in communication with the microfluidic channels, wherein said valve is controlled by the microcontroller.

7. System according to claim 5, wherein the control device comprises means for identifying the filling of at least one of the channels.

8. System according to claim 7, wherein the means for identifying comprises at least one capacitive sensor.

9. System according to claim 8, wherein the at least one capacitive filling level sensor comprises plural capacitive filling level sensors that share a common capacitor plate.

10. System according to claim 1, wherein the cartridge comprises at least one chamber, wherein the control device comprises a device for closing off and opening the at least one chamber.

11. System according to claim 1, wherein the cartridge comprises a PCR chamber, in which a PCR of the sample is able to be carried out.

12. System according to claim 1, wherein the cartridge comprises a detection chamber, in which DNA of the sample can be detected.

13. System according to claim 1, wherein the system comprises an evaluation unit that is separate from the control device.

14. System according to claim 1, wherein the control device comprises a serial interface for connecting the microcontroller to a computing unit.

15. System according to claim 1, wherein the control device comprises a sensor for identifying the type of the cartridge in the cartridge receptacle.

16. System according to claim 1, further comprising a water reservoir to dilute the sample, to dissolve dry reagents stored in the cartridge and to carry out flushing operations in the control device.

17. System according to claim 1, further comprising a display for representing the analysis results.

18. System according to claim 1, wherein the control device comprises a power supply unit.

19. System according to claim 1, wherein at least one filling level sensor is provided that comprises an electrode above the cartridge and an electrode below the cartridge.

20. A system for the integrated and automated analysis of DNA or protein, comprising:
a cartridge to receive a sample to be analyzed, the cartridge containing a reagent for analysis of the sample;
a control device for controlling an analysis process, wherein the control device comprises:
a cartridge receptacle for receiving the cartridge with two parts;
a microcontroller for control and data acquisition; and
a chip module for detection of DNA or protein;
wherein as soon as the cartridge has been completely introduced the two parts are brought together and the cartridge is locked or clamped inbetween,
wherein the chip module is thermally coupled to a Peltier element,
wherein the Peltier element is connected to one of the parts of the cartridge receptacle, and
wherein the Peltier element and chip are biased against each other in a resilient fashion.

21. System according to claim 20, wherein the cartridge comprises a sample port, wherein the sample port is configured to enable the sample to be pipetted into the cartridge via the sample port.

22. System according to claim 20, wherein the cartridge is a single-use cartridge.

23. System according to claim 20, wherein the cartridge is in the form of a plastic card.

24. System according to claim 20, wherein the cartridge comprises a plurality of microfluidic channels.

25. System according to claim 24, wherein the control device comprises at least one valve arranged in communication with the microfluidic channels, wherein said valve is controlled by the microcontroller.

26. System according to claim 24, wherein the control device comprises means for identifying the filling of at least one of the channels.

27. System according to claim 26, wherein the means for identifying comprises at least one capacitive sensor.

28. System according to claim 27, wherein the at least one capacitive filling level sensor comprises plural capacitive filling level sensors that share a common capacitor plate.

29. System according to claim 20, wherein the cartridge comprises at least one chamber, wherein the control device comprises a device for closing off and opening the at least one chamber.

30. System according to claim 20, wherein the cartridge comprises a PCR chamber, in which a PCR of the sample is able to be carried out.

31. System according to claim 20, wherein the cartridge comprises a detection chamber, in which DNA of the sample can be detected.

32. System according to claim 20, wherein the system comprises an evaluation unit that is separate from the control device.

33. System according to claim 20, wherein the control device comprises a serial interface for connecting the microcontroller to a computing unit.

34. System according to claim 20, wherein the control device comprises a sensor for identifying the type of the cartridge in the cartridge receptacle.

35. System according to claim 20, further comprising a water reservoir to dilute the sample, to dissolve dry reagents stored in the cartridge and to carry out flushing operations in the control device.

36. System according to claim 20, further comprising a display for representing the analysis results.

37. System according to claim 20, wherein the control device comprises a power supply unit.

38. System according to claim 20, wherein at least one filling level sensor is provided that comprises an electrode above the cartridge and an electrode below the cartridge.

* * * * *